US005696104A

United States Patent [19]
Demarchez et al.

[11] Patent Number: 5,696,104
[45] Date of Patent: Dec. 9, 1997

[54] PROCESS FOR IDENTIFYING RXR-RECEPTOR-AGONIST COMPOUNDS

[75] Inventors: Michel Demarchez, Le Bar sur Loup; André Jomard, Saint Vallier de Thiey, both of France

[73] Assignee: Centre International de Recherches Dermatologiques Galderma, Valbonne, France

[21] Appl. No.: 665,866

[22] Filed: Jun. 19, 1996

[30] Foreign Application Priority Data

Jun. 19, 1995 [FR] France .................. 95-07301

[51] Int. Cl.⁶ .............. A61K 31/59; A61K 31/19; A61K 31/20
[52] U.S. Cl. .............. 514/167; 514/557; 514/558; 514/559
[58] Field of Search .............. 514/167, 557, 514/558, 559

[56] References Cited

U.S. PATENT DOCUMENTS

| | | | |
|---|---|---|---|
| 5,399,586 | 3/1995 | Davies et al. | 514/448 |
| 5,455,265 | 10/1995 | Chandraratna | 514/448 |
| 5,552,271 | 9/1996 | Pfahl et al. | 435/6 |

FOREIGN PATENT DOCUMENTS

| | | |
|---|---|---|
| 608532 | 8/1994 | European Pat. Off. . |
| 91/12880 | 6/1994 | WIPO . |

OTHER PUBLICATIONS

Reichert, U. & B. Shroot (ED.) Pharmacology & The Skin, vol. 3, pp. 139–140 (1989).
Reichert, U. & B. Shroot (ED). Pharmacology & The Skin, vol. 3, pp. 98–99 (1989).
Leukemia, 1994, vol. 8, Suppl. 3, pp. 1–10.
Archives Of Biochemistry & Biophysics, 1994, vol. 314, pp. 82–89.
Database WPI, Sec. Ch. Wk 9515, (1996).
Database Dissertation Abstracts, Univ. Microfilms Int., Nuclei Acids Res. Nov. 3, 1993, vol. 21, pp. 12131–12137 (1993).
Biochem. Biophys. Res. Commun., vol. 204, pp. 498–504 (1994).
Journal Of Medical Chemistry, 1995, vol. 38, No. 15, pp. 2820–2829.
J. Biol. Chem. vol. 270, No. 51, pp. 30765–30772 (1995).

Primary Examiner—Kevin E. Weddington
Attorney, Agent, or Firm—Burns, Doane, Swecker & Mathis, L.L.P.

[57] ABSTRACT

The present invention relates to a process for identifying RXR-agonist molecules, characterized in that it comprises the following steps: (i) a sufficient amount of a compound which is an active ligand for at least one receptor of the super-family of steroidal/thyroidal receptors, other than an RXR-receptor-specific ligand, and which can heterodimerize with the RXRs, is applied topically to a part of the skin of a mammal, (ii) a molecule capable of having an RXR-agonist activity is administered systemically or topically to this same mammal, or to this same part of the skin of the mammal, before, during or after step (i), and (iii) the response on that part of the skin of the mammal thus treated is evaluated.

14 Claims, No Drawings

PROCESS FOR IDENTIFYING RXR-RECEPTOR-AGONIST COMPOUNDS

BACKGROUND OF THE INVENTION

Technical Field of the Invention

The present invention relates to a process for identifying RXR-receptor-agonist compounds using a mammal, such as a rodent (rat, guinea pig, hamster, rabbit, mouse, etc.).

It is known that all-trans-retinoic acid is a powerful modulator (i.e. an inhibitor or, on the other hand, a stimulator, depending on the nature of the cells treated) of the differentiation and proliferation of many normal or transformed cell types. For example, it inhibits the differentiation of epithelial cells, such as epidermal keratinocytes. It also inhibits the proliferation of many transformed cells, such as melanoma cells.

Generally speaking, it is known that all-trans-retinoic acid acts on cell differentiation and proliferation by interacting with nuclear receptors known as RARs (retinoic acid receptors) contained in the cell nucleus. After binding of the ligand (i.e. the all-trans-retinoic acid), these receptors interact with the promoter region of genes controlled by retinoic acid at the level of specific response elements. In order to bind to the response elements, the RARs heterodimerize with receptors of another type known as RXRs, the natural ligand of RXRs being 9-cis-retinoic acid. RXRs are considered to be "master regulatory proteins" since they interact to form heteromers, as in the case of the RARs, with other members of the super family of steroidal/thyroidal receptors, such as the vitamin D3 receptor (VDR), the triiodothyroxin receptor (TR) and the PPARs (peroxisome proliferator activated receptors).

Bearing in mind the biological activities mentioned above, the advantage of finding novel RXR-receptor-agonist compounds will be appreciated. Thus, many patents and publications have already described the advantage of using these compounds in the pharmaceutical field and more particularly the dermatological field.

Many synthetic structural analogues of all-trans-retinoic acid or of 9-cis-retinoic acid, commonly referred to as "retinoids", have been described in the literature to date. Some of these molecules are capable of binding and activating (agonists) or, conversely, of deactivating (antagonist) specifically RARs or, on the other hand, RXRs. Lastly, other analogues have no particular selectivity with respect to these various receptors. In this connection, and as an example, 9-cis-retinoic acid activates both RARs and RXRs, without any appreciable selectivity for either of these receptors (non-specific ligand), whereas all-trans-retinoic acid itself selectively activates RARs (RAR-specific antagonist).

In mice, it has been shown that the administration only of all-trans-retinoic acid topically induces a dose-dependent response of epidermal proliferation, with a maximum response four days after the application ("Retinoic acid provokes a regeneration-like proliferative response in murine epidermis" Arch. Dermatol. Res. 1992, 284: 418–423). In accordance with this result, the response to a topical application of all-trans-retinoic acid on mouse ear is reflected, in particular, by an increase in thickness of the mouse ear. This increase in mouse ear thickness seems to be due to an increase in the thickness of the epidermis and to the appearance of a dermal oedema. This response can thus readily be measured using a machine, such as the oditest, the response being at its maximum on the fifth and sixth days after the application.

Conversely, under the same operating conditions, RXR-specific ligands applied alone topically to mouse ear or orally do not induce any clinical effect.

The Applicant has just discovered that the response of the skin of a mammal to the topical application of a compound which is an active ligand for at least one receptor of the super-family of steroidal/thyroidal receptors, other than an RXR-receptor-specific ligand, and which can heterodimerize with the RXRs, may be synergized by the systemic or topical application of an RXR agonist.

Thus, the object of the present invention is to propose a simple process for identifying RXR-agonist molecules.

This and other objects are achieved by the present invention which relates to a process for identifying RXR-agonist molecules, characterized in that it comprises the following steps: (i) a sufficient amount of at least one compound which is an active ligand for at least one receptor of the super-family of steroidal/thyroidal receptors, other than an RXR-receptor-specific ligand, and which can heterodimerize with the RXRs, is applied topically to a part of the skin of a mammal, (ii) a molecule capable of having an RXR-agonist activity is administered systemically or topically to this same mammal, or to this same part of the skin of the mammal, before, during or after step (i), and (iii) the response on that part of the skin of the mammal thus treated is evaluated and compared with the response obtained on this same part of skin treated by step (i) only.

Thus, when the molecule administered is an RXR agonist, the thickness of the part of the skin of the mammal thus treated with a molecule which is an active ligand for at least one receptor of the super-family of steroidal/thyroidal receptors, other than an RXR-receptor-specific ligand, and which can heterodimerize with the RXRs, increases. It is thus possible to speak of a synergism of response, since the molecule capable of having an agonist activity for the RXRs to be tested induces no clinical effect when it is applied alone via the topical route.

In practice, the mammal is a rodent such as a mouse, a rat, a guinea pig, a hamster or a rabbit.

The part of the mammal skin used can be any part of the mammal's body.

The response on that part of the skin of the mammal thus treated and to be evaluated corresponds to a clinical modification of the skin. In general, this response to be evaluated corresponds to a modification in the thickness of the part of the skin thus treated.

Thus, the thickness of the part of the skin thus treated may be measured by any method known per se.

When the part of the skin used is smooth, its thickness may be measured by folding it.

In a more practical manner, the skin of the ear is used. The thickness of the ear may then be measured by an oditest.

Obviously, the evaluation of step (iii) corresponds to a measurement of the response of the part of the skin thus treated and to a comparison of this measurement with that of the response of this same part of the treated skin, under the same conditions, with the same active ligand for at least one receptor of the super family of steroidal/thyroidal receptors, other than an RXR-receptor-specific ligand, which can heterodimerize with the RXRs alone.

Among the active ligands for at least one receptor of the super-family of steroidal/thyroidal receptors, other than an RXR-receptor-specific ligand, which can heterodimerize with the RXRs, mention may be made in particular of RAR (retinoic acid receptor) ligands, of VDR (vitamin D3 receptor) ligands, of PPAR (peroxisome proliferator activated receptor) ligands and of TR (triiodothyroxine receptor) ligands.

RAR agonists are preferably used as active ligands for at least one receptor of the super-family of steroidal/thyroidal receptors, other than an RXR-receptor-specific ligand, which can heterodimerize with the RXRs.

Among the RAR agonists which may be mentioned more particularly are:
all-trans-retinoic acid,
2-(5,6,7,8-tetrahydro-5,5,8,8,-tetramethyl-2-naphthyl)-6-benzo[b]thiophenecarboxylic acid,
4-[(5,6,7,8-tetrahydro-5,5,8,8,-tetramethyl-2-naphthyl) carboxamido]benzoic acid,
4-[(5,6,7,8-tetrahydro-5,5,8,8-tetramethyl-2-naphthyl) carbamoyl]benzoic acid.

Examples of VDR-receptor ligands which may be mentioned are the following vitamin D derivatives:
1α,25-dihydroxyvitamin D3,
1α-hydroxyvitamin D3,
25-hydroxyvitamin D3,
1α,25-dihydroxyvitamin D2,
1α,24-dihydroxyvitamin D2

Among the PPAR-receptor-specific ligands which may be mentioned in particular are bromopalmitic acid and analogues thereof.

In the following and in the foregoing text, the expression "via the topical route" is understood to refer to any technique for administering a product by direct application of this product to a surface (or external) part of the body, and the term "systemically" is understood to refer to any technique for administering a product via a route other than a topical route, for example enterally and/or parenterally. In the case of the systemic route, the oral route is preferably used.

The sufficient amount of at least one active ligand for at least one receptor of the super-family of steroidal/thyroidal receptors, other than an RXR-receptor-specific ligand, which can heterodimerize with the RXRs to be applied, corresponds to that at which an oedematous response of the treated part of the skin of the mammal after steps (i) and (ii) (that is to say after application of the two compounds) is observed. In practice, this sufficient amount corresponds to the maximum limit at which no further response of the treated part of the skin of the mammal is observed after step (i) (that is to say after the application only of the active ligand for at least one receptor of the super-family of steroidal/thyroidal receptors, other than an RXR-receptor-specific ligand, which can heterodimerize with the RXRs). Thus, preferably and depending on the nature of the compound used, this amount is in the range between 0.0001% and 5% by weight per unit volume of solution applied.

Several examples intended, on the one hand, to demonstrate the effects associated with the present invention and, on the other hand, to illustrate various concrete formulations in accordance with the invention will now be given, without any limitation whatsoever being implied.

EXAMPLE 1

The test used is thus that of mouse-ear oedema induced by topical application of 2-(5,6,7,8-tetrahydro-5,5,8,8-tetramethyl-2-naphthyl)-6-benzo[b]thiophenecarboxylic acid (all-trans-retinoic acid analogue) at a concentration of 0.003% on a weight per unit volume basis. According to this model, a topical application of 2-(5,6,7,8-tetrahydro-5,5,8,8-tetramethyl-2-naphthyl)-6-benzo[b]thiophenecarboxylic acid to the ear gives rise to an inflammation which is characterized by an increase in the thickness of this ear, this increase becoming maximal at the end of 5 days after the application. The response may thus be quantified by measuring the thickness of the ear by an oditest.

According to this model, in a preliminary study, the maximum dose of 2-(5,6,7,8-tetrahydro-5,5,8,8-tetramethyl-2-naphthyl)-6-benzo[b]thiophenecarboxylic acid to be applied and which induces no increase in thickness of the mouse ear was determined. This is the dose which is used during the following procedure.

The exact procedure is as follows: 10 mice are first treated with 2-(5,6,7,8-tetrahydro-5,5,8,8-tetramethyl-2-naphthyl)-6-benzo[b]thiophenecarboxylic acid (compound A), carrying out a topical application to one of their ears at time t=0 with 20 ml of an acetone solution comprising 0.003% on a weight per unit volume basis of compound A. 4-[(3,5,5,8,8-Pentamethyl-5,6,7,8-tetrahydro-2-naphthyl)carbonyl] benzoic acid (compound B) in oil of cremophor type (EL 25%) is given orally to 5 (=group 2) out of 10 of the mice thus treated, from t=0 and once a day for 11 days. The 5 mice which have not been given compound B constitute group 1. The response is quantified by measuring the thickness of the ear at t=5 or 6 days. The results are then expressed as a % of the synergistic effect, calculated in the following way:

$$\frac{\text{mouse-ear thickness (Group 2)} - \text{mouse-ear thickness (Group 1)}}{\text{mouse-ear thickness (Group 1)}} \times 100$$

Moreover, compound B is described as being an RXR-specific antagonist (see: Marcus F. Boehm et al., J. Med. Chem. 1994, 37, 2930–2941).

The results obtained are collated in Table 1 below.

TABLE 1

| Topical route | Dose (% w/v) | Oral route | Dose (mg/kg) | Synergistic effect (%) |
|---|---|---|---|---|
| Compound A | 0.003 | Compound B | 0 | 0 |
| Compound A | 0.003 | Compound B | 10 | 73 |
| Compound A | 0.003 | Compound B | 30 | 118 | w/v means weight per unit volume.

Furthermore, under the same operating conditions, the topical application of an RXR-specific ligand alone, such as compound B, induces no response.

Thus, it is clearly demonstrated by means of this test that the combination of an RAR-receptor ligand with a compound known to be an RXR-agonist molecule considerably increases the response when compared with the response induced by topical application only of an RAR-receptor ligand.

EXAMPLE 2

Exactly the same test as in Example 1 is performed, except that, instead of being administered orally, compound B is applied topically in an acetone solution at a dose of 0.1% by weight per unit volume on an ear already treated with compound A at a concentration of 0.01% or 0.003% w/v.

The results obtained are collated in Table 2 below.

TABLE 2

| Topical route | Dose (% w/v) | Topical route | Dose (mg/kg) | Synergistic effect (%) |
|---|---|---|---|---|
| Compound A | 0.01 | Compound B | 0.1 | 159 |
| Compound A | 0.003 | Compound B | 0.1 | 541 | w/v means weight per unit volume.

EXAMPLE 3

Exactly the same test as in Example 1 is performed, except that compound B is replaced by a compound C, (E)-2-[2-(3,5,5,8,8-pentamethyl-5,6,7,8-tetrahydro-2-naphthyl-1-propenyl]-4-thiophenecarboxylic acid, and is applied topically as in Example 2.

Compound C is described as being an RXR-specific agonist in patent application WO 94/17796 filed by the company Allergan.

The results obtained are collated in Table 3 below.

TABLE 3

| Topical route | Dose (% w/v) | Topical route | Dose (mg/kg) | Synergistic effect (%) |
|---|---|---|---|---|
| Compound A | 0.01 | Compound C | 0.1 | 169 |
| Compound A | 0.003 | Compound C | 0.1 | 617 | w/v means weight per unit volume.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for identifying an RXR-agonist molecule which method comprises the following steps:
   (i) applying topically to a skin site of a mammal a sufficient amount of at least one compound which is an active ligand for at least one receptor of the super-family of steroidal/thyroidal receptors, other than an RXR-receptor-specific ligand, and which ligand can heterodimerize with the RXR;
   (ii) administering systemically or topically to said same mammal and further to the same skin site if topically administered, a molecule which putatively comprises RXR-agonist activity before, during or after step (i); and
   (iii) evaluating the skin response at said site after steps (i) and (ii), and comparing such response to the response obtained at a skin site when such skin site is treated only according to step (i) and, based on this comparison, determining whether the topically or systemically administered compound is an RXR-agonist molecule.

2. A process according to claim 1, wherein the mammal is a rodent.

3. A method according to claim 1, wherein rodent is selected from the group consisting of mice, rats, guinea pigs, hamsters and rabbits.

4. A method according to claim 1, wherein the skin site of the mammal treated in step (i) comprises the skin of the ear.

5. A method according to claim 1, wherein the skin response evaluated in step (iii) comprises measuring whether there is a modification in the thickness of the skin at the skin site that the compound in step (i) is applied after step (i) alone, or in combination with step (ii).

6. A method according to claim 1, wherein the active ligand for at least one receptor of the super-family of steroidal/thyroidal receptors in step (i) is selected from the group consisting of RAR (retinoic acid receptor) ligands, VDR (vitamin D3 receptor) ligands, PPAR (peroxisome proliferator activated receptor) ligands, and TR (triiodothyronine receptor) ligands.

7. A method according to claim 6, wherein the active ligand in step (i) is an RAR agonist.

8. The method according to claim 7, wherein the RAR-agonist is selected from the group consisting of all-trans-retinoic acid, 2-(5,6,7,8-tetrahydro-5,5,8,8,-tetramethyl-2-naphthyl)-6-benzo[b]thiophenecarboxylic acid, 4-[(5,6,7,8-tetra-hydro-5,5,8,8,-tetramethyl-2-naphthyl)carboxamido] benzoic acid, 4-[(5,6,7,8-tetrahydro-5,5,8,8-tetramethyl-2-naphthyl)carbamoyl]benzoic acid.

9. A method according to claim 6, wherein the active ligand is a VDR ligand.

10. A method according to claim 9, wherein the VDR ligand is selected from the group consisting of 1α,25-dihydroxyvitamin D3, 1α-hydroxyvitamin D3, 25-hydroxyvitamin D3, 1α,25-dihydroxyvitamin D2, 1α,24-dihydroxyvitamin D2.

11. A method according to claim 6, wherein the active ligand is a PPAR ligand.

12. A method according to claim 11, wherein the PPAR ligand is bromopalmitic acid.

13. A method according to claim 1, wherein the putative RXR-agonist molecule in step (ii) is systemically administered.

14. A method according to claim 13, wherein systemic administration comprises oral administration.

* * * * *

UNITED STATES PATENT AND TRADEMARK OFFICE
CERTIFICATE OF CORRECTION

PATENT NO. : 5,696,104
DATED : December 9, 1997
INVENTOR(S) : Michel DEMARCHEZ et al.

It is certified that error appears in the above-indentified patent and that said Letters Patent is hereby corrected as shown below:

At Column 1, line 49, delete "antagonist" and insert therefor --agonist--; .

At Column 4, line 9, delete "ml" and insert therefor --$\mu$l--;

line 24, delete "antagonist" and insert therefor --agonist--;

Table 2, delete "(mg/kg)" and insert therefor --(w/v)--;

At Column 5, Table 3, delete "(mg/kg)" and insert therefor --(w/v)--;

Signed and Sealed this

Nineteenth Day of May, 1998

Attest:

BRUCE LEHMAN

Attesting Officer

Commissioner of Patents and Trademarks